United States Patent [19]

Jordan

[11] Patent Number: 4,474,709
[45] Date of Patent: Oct. 2, 1984

[54] REMOVAL OF OXAZOLE FROM ACETONITRILE

[75] Inventor: Stephen P. Jordan, Beaumont, Tex.

[73] Assignee: E. I. Du Pont de Nemours and Company, Wilmington, Del.

[21] Appl. No.: 392,790

[22] Filed: Jun. 28, 1982

[51] Int. Cl.$^3$ .................. C07C 120/14; C07C 121/18
[52] U.S. Cl. ................................ 260/465.3; 548/235
[58] Field of Search ................ 260/465.1, 465.3; 548/235

[56] References Cited

U.S. PATENT DOCUMENTS

| | | | |
|---|---|---|---|
| 3,201,451 | 8/1965 | Idol et al. ........................ | 260/465.1 |
| 3,203,975 | 8/1965 | Sobel et al. ..................... | 260/465.1 |
| 3,267,128 | 7/1963 | Pursell ............................. | 260/465.3 |
| 3,301,770 | 9/1963 | Di Cio et al. .................... | 203/54 |
| 3,352,764 | 5/1966 | Tyler ................................ | 203/42 |
| 3,451,899 | 6/1969 | Sheely ............................. | 203/69 |
| 3,522,268 | 7/1970 | Hall et al. ........................ | 260/307 |
| 3,524,875 | 8/1970 | Hadley et al. ................... | 260/465.3 |
| 3,541,131 | 11/1970 | Darcas et al. .................... | 548/235 X |
| 3,574,687 | 4/1971 | Darcas et al. .................... | 548/235 |
| 3,686,263 | 8/1972 | Maute ............................. | 260/465.3 |
| 3,697,576 | 10/1972 | Allirot et al. .................... | 548/235 X |
| 3,801,622 | 4/1974 | Kimoto et al. .................. | 260/465.9 |
| 4,061,858 | 12/1977 | Wild et al. ...................... | 526/67 |
| 4,119,497 | 10/1978 | Ocampo et al. ................. | 203/29 |
| 4,177,210 | 12/1979 | Vanderkooi et al. ........... | 548/235 X |
| 4,204,915 | 5/1980 | Kurata et al. ................... | 203/2 |
| 4,208,329 | 6/1980 | Smiley ............................. | 548/239 |
| 4,211,722 | 7/1980 | Smiley ............................. | 548/235 X |
| 4,237,303 | 12/1980 | Gatling ........................... | 548/235 |
| 4,246,417 | 1/1981 | Tsao ................................ | 546/286 |
| 4,269,667 | 5/1981 | Landis ............................. | 203/76 |
| 4,294,665 | 10/1981 | Issei et al. ....................... | 203/50 |
| 4,308,108 | 12/1981 | Higuchi et al. ................. | 203/37 |

FOREIGN PATENT DOCUMENTS 1156713  7/1969  United Kingdom .
1500329  2/1978  United Kingdom .

*Primary Examiner*—Joseph Paul Brust

[57] ABSTRACT

Removing oxazole from acetonitrile using chlorine.

8 Claims, No Drawings

REMOVAL OF OXAZOLE FROM ACETONITRILE

BACKGROUND OF THE INVENTION

1. Field of the Invention

This invention concerns the purification of acetonitrile and, more particularly, the removal of oxazole from acetonitrile by contacting the oxazole/acetonitrile mixture with molecular chlorine.

2. Description of the Prior Art

Oxazole has been removed from nitriles by a variety of techniques. U.S. Pat. No. 4,208,329 issued June 17, 1980 discloses a technique for removing oxazole from acrylonitrile by contacting the nitrile with sulfuric acid thereby forming oxazole sulfate and subsequently separating that sulfate from the acrylonitrile. U.S. Pat. No. 3,524,875 issued Aug. 18, 1970 discloses the removal of oxazole from acrylonitrile by distillation while U.S. Pat. No. 3,686,263 issued Aug. 22, 1972 removes oxazole by complexing that compound with certain metal salts.

U.S. Pat. No. 4,308,108 issued Dec. 29, 1981 discloses numerous processes for the purification of acetonitrile including the removal of hydrogen cyanide, allyl alcohol, oxazole and water, e.g., by alkali treatment and extractive distillation. The patentees disclose that oxazole is removed from acetonitrile by subjecting the crude acetonitrile to extractive distillation in the presence of minor amounts of water. This technique is effective but requires large amounts of energy.

Oxazole is recovered from an aqueous acetonitrile solution by complexing the oxazole with an inorganic cadmium salt and subsequently contacting the resultant precipitate with an acid, e.g., hydrochloric acid according to the teachings of U.S. Pat. No. 3,522,268 issued on July 28, 1970. A process for the recovery of unreacted alpha-unsaturated nitriles from a gas phase chlorination by contacting the unreacted nitriles with iron, aluminum or their oxides and thereafter separating the nitrile from the iron or aluminum is disclosed in U.S. Pat. No. 3,801,622 issued on Apr. 2, 1974. U.S. Pat. No. 3,203,975 issued on Aug. 31, 1965 discloses a process for the removal of contaminates from nitrogen containing, water soluble compounds, such as acetonitrile, by contacting the nitrile with calcium chloride, acidifying the resultant mixture, separating the resultant oil layer and further treating the oil layer with additional calcium chloride to finally obtain a purified nitrile.

British Pat. No. 1,500,329 published on Feb. 8, 1978 discloses a process for the removal of allyl alcohol from acetonitrile by contacting the acetonitrile with chlorine. Although the patentees recognize that other impurities may be present which react more rapidly with the chlorine than does allyl alcohol, there is no disclosure or suggestion that oxazole is present or is reacted.

British Pat. No. 1,156,713 published on July 2, 1969 discloses a process for the recovery of oxazole from aqueous solution together with acetonitrile by treating the solution with a suitable inorganic salt such as mercuric chloride, calcium chloride, etc. and thereafter recovering oxazole from the oxazole/inorganic salt complex.

SUMMARY OF THE INVENTION

A process for removing oxazole from a mixture of acetonitrile and oxazole which comprises or consists essentially of contacting the acetonitrile in a liquid state with molecular chlorine and thereafter separating the oxazole-chlorine reaction products from the thus treated acetonitrile.

It is preferred to contact the acetonitrile with molecular chlorine at a temperature in the range 20°–80° C. and after the contact with chlorine, to then contact the thus treated acetonitrile with an aqueous solution of base to extract the reaction products from the acetonitrile and permit recovery of relatively pure nitrile. The basicity of the aqueous solution should be controlled such that the pH is in the range of 7–14 and the temperature is maintained at less than 60° C. so that excessive acetonitrile is not hydrolyzed.

DETAILED DESCRIPTION OF THE INVENTION

Acetonitrile has found increasing use as a solvent in many areas, such as pharmaceutical, agricultural and particularly analytical since it does not absorb ultraviolet rays. In several applications and, particularly in analytical applications, the acetonitrile must be exceptionally pure, i.e., greater than 99.0%. A significant amount of the acetonitrile which is used in the above discussed applications is obtained as a by-product stream from the manufacture of acrylonitrile by the ammoxidation of propylene. A typical stream from such a process would have the following approximate composition:

| Compound | Concentration (% by weight) |
|---|---|
| Water | 16 |
| Oxazole | 2 |
| Acrylonitrile | 1 |
| Allyl Alcohol | 0.5 |
| Propionitrile | 1.0 |
| Crotononitrile | 0.2 |
| Hydrogen Cyanide | 1.0 |
| Pyridine | 0.1 |
| Acetonitrile | 78.2 |

No particular pretreatment of the crude acetonitrile stream is required prior to contacting it with chlorine. However, in the preferred embodiment of the present invention both the hydrogen cyanide and the acrylonitrile are removed prior to the chlorination in order to reduce the number of possible chlorinated products of these materials in the final product. Hydrogen cyanide can be removed by known methods, e.g., by contacting the acetonitrile with caustic. The acrylonitrile may be removed, for example, by reaction with aliphatic amines.

The chlorine employed in the present process must be molecular chlorine, i.e., $Cl_2$. Preferably the chlorine gas is dissolved in or bubbled through the reaction medium.

The temperature at which the chlorination of the oxazole is conducted is not critical. The chlorination is an exothermic reaction and should be controlled within reasonable limits to prevent degradation of the product. Temperatures in the range of about 5°–80° C. and preferably 20°–70° C. are preferred.

The method of contacting the reactants is also not critical to the present invention so long as the chlorine and oxazole are brought into intimate contact, e.g., by thorough mixing. The reaction rate of chlorine with oxazole is very rapid, i.e., on the order of about 1 to about 3 minutes at a temperature in the range 25°–50° C. and therefore long holdup times are not required to effect substantially complete reaction of the chlorine and oxazole.

The amount of chlorine which is required to react with essentially all of the oxazole in the acetonitrile will vary with the level of oxazole as well as the level of other impurities, e.g., allyl alcohol, acetone, etc. which are known to react with chlorine. One skilled in the art can readily determine the amount of chlorine which must be introduced to react with compounds other than oxazole by introducing chloride into the particular acetonitrile mixture to be treated and noting when the oxazole level begins to fall. At this point essentially all the other compounds have reacted with the chlorine. Chlorine addition is then continued until the oxazole is essentially completely reacted.

It is preferred to neutralize the acidic, chlorinated acetonitrile reaction product in order to permit lower cost materials of construction for subsequent processing apparatus. Base may be introduced in a variety of methods but is preferably introduced as an aqueous solution containing 30–50% by weight of the base. Essentially any base which will react with by-product HCl can be used. Such bases include alkali metal hydroxides, organic amines and quaternary ammonium hydroxides, etc. Examples of the foregoing bases include potassium hydroxide, lithium hydroxide, calcium hydroxide, barium hydroxide and tetramethyl ammonium hydroxide, etc.

The amount of base which is employed should be controlled to maintain the pH of the aqueous solution in the range 7–14 and preferably 10–12. This range of pH and a temperature in the range of 40°–60° C. while the base is in contact with the acetonitrile should be employed to provide the maximum removal of chlorinated reaction products while minimizing hydrolysis of the acetonitrile.

After contact with the aqueous base, the decanting of the organic, i.e., acetonitrile layer, from the aqueous layer allows the water content of the acetonitrile to be reduced. The water content of this organic layer can further be reduced using other drying techniques such as contacting the organic layer with calcium chloride or concentrated caustic.

After the optional drying, the acetonitrile is directed to a distillation where other impurities such as residual water and propionitrile, etc. are removed from the acetonitrile to provide an essentially 100% pure material.

The following examples are presented to illustrate but not to restrict the present invention. Parts and percentages are by weight unless otherwise noted.

EXAMPLE 1

Approximately 628 grams of crude acetonitrile containing 17.7% water, 1.01% oxazole, 0.29% allyl alcohol and 0.82% propionitrile were charged to 1 liter flask. Hydrogen cyanide had been removed from this acetonitrile by contacting the acetonitrile with excess aqueous caustic at ambient temperature and thereafter recovering the acetonitrile in a water azeotrope by standard distillation and acrylonitrile had been removed by contacting the azeotrope obtained as above with a slight excess of ethylene diamine (on acrylonitrile basis) at ambient temperature.

After the acetonitrile was charged to the flask approximately 22 grams of elemental chlorine gas was bubbled into the mixture over a period of 9 minutes while the mixture was slowly stirred and maintained at a temperature of 55° C.

After the chlorine in addition was complete, the chlorinated mixture was cooled to 25° C. and thereafter neutralized to a pH of 12.4 by the addition of 87 grams of a 50% aqueous solution of sodium hydroxide. Two phases had formed in the flask. The organic phase (approximately 547 grams) was decanted from the aqueous phase (approximately 174 grams) and found by analysis to contain 8.4% $H_2O$, 0% oxazole, 0% allyl alcohol, 0.91% propionitrile. The water level in the organic layer was reduced to about 4.0% by contacting the organic layer with 20 grams of calcium chloride following which the layer was placed in a one liter pot of a still having 40 plates and distilled at a head temperature of 81.5° C., a pot temperature of 82° C. and a reflux ratio of 6/1 to produce approximately 200 grams of acetonitrile which contained essentially no oxazole or allyl alcohol.

EXAMPLE 2

Approximately 200 grams of acetonitrile containing about 0.3% water, 0.08% oxazole, 0.21% allyl alcohol, and 0.32% propionitrile were charged to a 500 ml. flask. Approximately 0.85 gram of elemental chlorine gas was bubbled into the mixture over a period of four (4) minutes while the mixture was slowly stirred and maintained at a temperature of 29° C.

The above mixture was flash distilled using a one plate column at a head temperature of 81° C. to produce approximately 155 grams of acetonitrile which contained essentially no oxazole or allyl alcohol.

In one preferred embodiment of the present invention a crude acetonitrile stream is initially mixed with chlorine gas and introduced into a reactor to permit the chlorination to proceed. The reaction mixture is then cooled and contacted with aqueous caustic to neutralize the mixture to a pH in the range of 10–12.

After the neutralization, the mixture which has increased in temperature is directed to a heat exchanger to reduce its temperature and thereafter directed to a decanter where the aqueous and organic phases are separated. The organic phase containing the acetonitrile is further dried by contacting it with solid calcium chloride which results in the formation of an aqueous and organic phase.

The organic phase containing the acetonitrile is directed to a first distillation column where residual water is removed and recycled to the process following which the dry acetonitrile is then directed to a second distillation column where essentially pure acetonitrile is taken overhead and organic waste removed through the tails.

I claim:

1. A process for removing oxazole from acetonitrile which comprises contacting acetonitrile with molecular chlorine until essentially all of the compounds other than oxazole which are capable of reacting with the chlorine have reacted, additionally introducing at least 2.0 mols of molecular chlorine for each mol of oxazole at a temperature in the range 20°–80° C. until the oxazole is essentially completely reacted and separating the oxazole-chlorine reaction product from the thus treated acetonitrile.

2. The process of claim 1 wherein the oxazole-chlorine reaction product is separated from the acetonitrile by contacting the nitrile with an aqueous solution of a base and thereafter separating acetonitrile in the resulting organic phase and from the oxazole-chlorine reaction product in the resulting aqueous phase.

3. The process of claim 2 wherein the base is an alkali metal hydroxide and is introduced in amounts sufficient to maintain the ph of the aqueous solution in the range 7-14.

4. The process of claim 1 wherein the acetonitrile is obtained by the ammoxidation of propylene.

5. The process of claims 2, 3 or 4 wherein the temperature of the nitrile is maintained in the range 40°-60° C. during contact with the aqueous solution of base.

6. The process of claim 3 wherein the nitrile which has been contacted with the aqueous base is distilled.

7. A process for the separation of oxazole from a mixture comprising acetonitrile and oxazole prepared by the ammoxidation of propylene which comprises contacting the mixture with molecular chlorine until essentially all of the compounds other than oxazole which are capable of reacting with chlorine have reacted, additionally introducing at least 2.0 mols of molecular chlorine for each mol of oxazole at a temperature in the range 20°-80° C.; until the oxazole is essentially completely reacted, contacting the chlorine treated mixture with an aqueous solution containing 30-50% by weight of a base selected from the class consisting of sodium hydroxide, potassium hydroxide and mixtures thereof at a temperature in the range 40°-60° C. while maintaining the pH of the system in the range of 10-12; separating the resulting aqueous and organic phases and recovering acetonitrile from the organic phase.

8. The process of claim 3 wherein the pH is maintained in the range 10-12.

* * * * *